United States Patent [19]

Frazier

[11] 4,294,237

[45] Oct. 13, 1981

[54] SPLINT FOR REDUCING FRACTURES OF THE METACARPALS

[76] Inventor: Calvin H. Frazier, 1808 Verdugo Blvd., Glendale, Calif. 91208

[21] Appl. No.: 107,025

[22] Filed: Dec. 26, 1979

[51] Int. Cl.³ .............................................. A61F 5/10
[52] U.S. Cl. .................................... 128/77; 128/87 A
[58] Field of Search ..................... 128/77, 87 R, 87 A, 128/83, 89 R

[56] References Cited

U.S. PATENT DOCUMENTS

| | | | |
|---|---|---|---|
| 1,880,945 | 10/1932 | Ettinger | 128/83 X |
| 2,520,035 | 8/1950 | Goldberg | 128/87 A |
| 3,439,673 | 4/1969 | Sprecher | 128/87 R |
| 3,595,225 | 7/1971 | Beeman | 128/77 |
| 3,788,307 | 1/1974 | Kistner | 128/77 |

OTHER PUBLICATIONS

Granberry's Metacarpal and Phalanges Splint, DePuy Catalogue, 1943, p. 18.

Primary Examiner—John D. Yasko
Attorney, Agent, or Firm—William C. Conkle

[57] ABSTRACT

A splint for reducing fractures of the metacarpals having a foundation lying adjacent the ulnar side of the hand and extending over the dorsum and the palm. An adjustable pressure plate is advanced toward the dorsum where its force reduces the apex of the broken metacarpal. The foundation is held in place on the hand by an adjustable strap.

9 Claims, 4 Drawing Figures

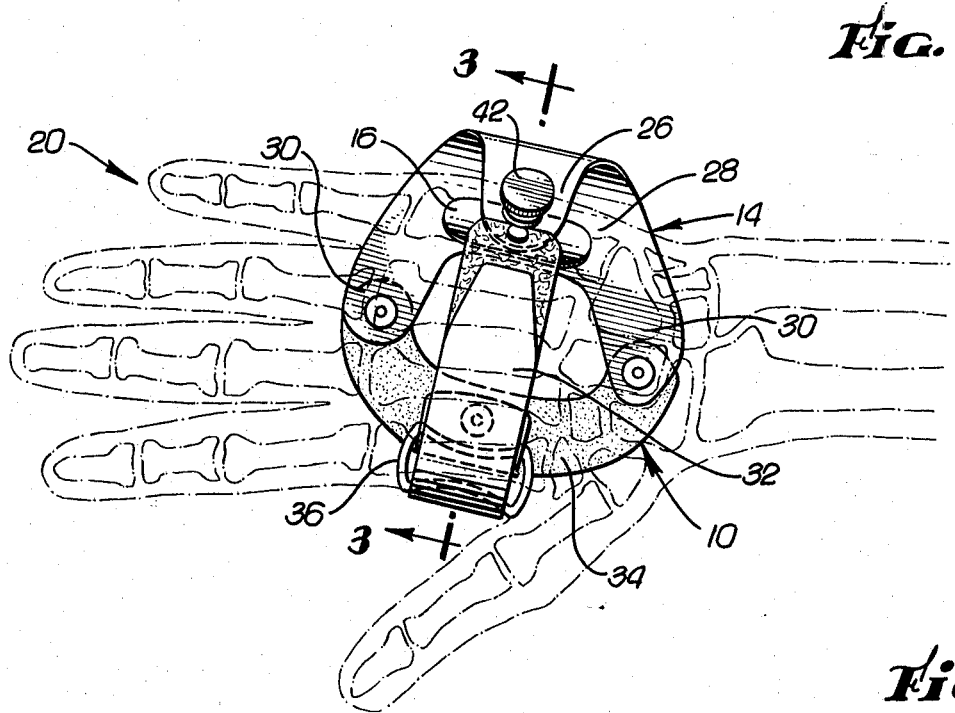
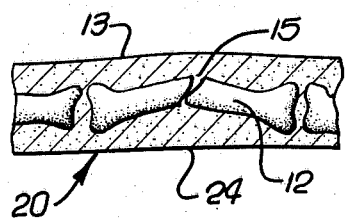
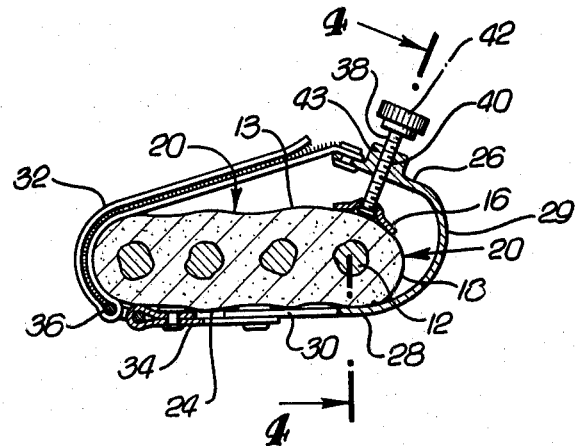
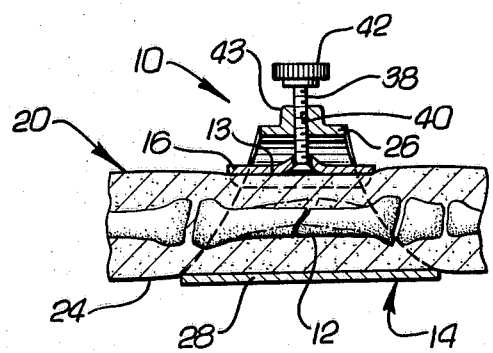

SPLINT FOR REDUCING FRACTURES OF THE METACARPALS

BACKGROUND OF THE INVENTION

This invention relates generally to an improvement in externally applied bone engaging splints and particularly to a splint for reducing a fracture to the fifth metacarpal.

Fractures to the fifth metacarpal are a frequent occurrence. The bone structure of the hand generally produces a fracture in which the bone tends to break in a direction toward the dorsum. After the break, the ends of the broken metacarpal tend to form a peak extending outwardly of the dorsum, such fractures especially those occurring about one centimeter inward from the distal end of the fifth metacarpal are called "boxer's fractures." When the metacarpal heals in this peaked position there results a cosmetic deformity in the hand, as well as a structural deformity.

Splints and bandages in general use are not satisfactory for reducing boxer's fractures since they cannot place sufficient reducing force on the broken metacarpal to restore it to its proper position. Moreover, the large cumbersome splints presently in use immobilize the ring and little finger as well as the wrist when they are used to reduce fractures of the metacarpal. Immobilizing the ring and little finger is undesirable if it can be avoided.

Hence, there existed a need for a splint which could hold a broken metacarpal in a proper healing position without immobilizing the ring and little fingers while it reduces the fractured metacarpal. Such a splint should ideally be small, should be formed to fit to the shape of the hand thereby preventing it from slipping. The splint should have an adjustable means of applying pressure directly to the broken metacarpal. The splint should be comfortable to wear, lightweight and easy to manufacture and not unnecessarily unsightly. The present invention fulfills these needs.

SUMMARY OF THE INVENTION

Briefly, and in general terms, the present invention provides a new apparatus for, and method of using the apparatus in, reducing fractures of the metacarpals especially "boxer's fractures" of the fifth metacarpal.

The present invention includes a foundation configured to be attached to the ulnar side (the side opposite the thumb) of the hand. One end of the foundation extends over the dorsum and mounts an adjustable pressure plate which can be manually advanced to push the broken metacarpal back into its proper position. The other end of the foundation extends over the palm and acts to support the splint in position. The foundation is held in place on the hand by an adjustable strap.

More particularly, the adjustable pressure plate is a small curved plate rotatably mounted on an end of a threaded shaft. The shaft passes through an aperture in a portion of the foundation adjacent the dorsum, the foundation acting to hold the shaft and pressure plate in position over the fractured metacarpal. A knob atop the shaft permits screw adjustment of the shaft and plate.

The foundation is held in place both by being held by an adjustable attaching strap and by its shape which is complementarily to the shape of a hand. One end of the VELCRO covered strap is attached to the foundation and the other end is passed through an eyelet and looped back to engage itself and form adjustable attachment. Two projecting sections extend outwardly from the part of the foundation adjacent the palm. These projecting sections rest against the palm and act to position the foundation on the hand. To the projections is attached a flexible fabric connector joining the projections and having on the other side the eyelet through which the strap passes.

The above and other objects and advantages of this invention will become apparent from the following more detailed description, when taken in conjunction with the accompanying drawings of illustrative embodiments.

BRIEF DESCRIPTION OF THE DRAWINGS

FIG. 1 is a fragmentary longitudinal sectional view of a human hand showing a broken fifth metacarpal bending toward the dorsum of the hand;

FIG. 2 is a dorsum view of a right hand showing a splint of the invention placed on the hand;

FIG. 3 is a cross section view taken along line 3—3 in FIG. 2 and showing the splint in place on the hand; and FIG. 4 is a sectional view taken along line 4—4 in FIG. 3 and showing the splint and the hand, the hand having a broken metacarpal shown in phantom line and the metacarpal reduced by the splint shown in solid line.

DETAILED DESCRIPTION

As shown in the drawings for the purposes of illustration, the invention is embodied in a splint 10 for reducing fractures of the fifth metacarpal 12, especially fractures that are located about 1½ centimeters from the distal end of the metacarpal, such fractures being commonly called "boxer's fracture." As is shown in FIG. 1, the structure of a human hand 20 causes such a broken fifth metacarpal 12 to bow toward the dorsum 13 of the hand and causes the broken ends of the metacarpal bone to form a peak 15 at the breakpoint. FIGS. 2, 3, and 4 illustrate the general construction and use of the splint 10, including a foundation 14 and an adjustably positionable padded pressure plate 16 that is used to press the peak 15 of the fractured metacarpal 12 inwardly away from the dorsum 13 and back into its natural shape thereby allowing the fractured metacarpal to mend in its natural shape.

In accordance with the present invention, the rigid foundation 14 is adjustably secured to the hand 20 and mounts the adjustable pressure plate 16 that presses against the peak 15 of the fracture, and moves the fractured bones back into their natural position.

More particularly, the foundation 14 is a generally rigid metallic plate having a longitudinal cross section that is curved so as to conform to the configuration of an ulnar 18 side of a human hand 20. The foundation has generally planar portions one extending over the dorsum 13 and the other over the palm 24. A reducing portion 26 of the foundation 14 overlies the fifth metacarpal, while a support end 28 of the foundation 14 lies on the other side of the hand adjacent to the palm 24. A longitudinal cross-section of the foundation 14, such as is shown in FIG. 3, has a generally C-shaped curved support portion 29 connecting the reducing portion 26 and the support end 28.

To enable the splint 10 to fit comfortably on the hand 20, the reducing portion 26 has relatively narrow width, the dimension parallel the axis of the metacarpals, while the support end 28 is significantly wider and is adapted to rest against the meaty part of the palm 24. In the presently preferred embodiment, the reducing portion 26 is about one inch wide and the support end 28 is about four inches wide. In order to make the splint more comfortable to the user, the support end has two projecting sections 30, one at each end of the connecting portion 28 to which a securing strap 32, described in more detail below, is attached. The projecting sections 30 overlie the meaty part of the palm 24, each section 30 is almost one inch wide and extends about one inch out from the support end 28. If the foundation 14 were flattened, its shape would, in general, be a triangle whose apex would be the reducing portion 26 and whose base would be the support end 28. It will be appreciated that a foundation 13 configured to fit a right hand is slightly different from one configured to fit a left hand, but that the two foundations are mirror images of one another.

The foundation 14 is held in place on the hand 20 of the patient by means of a flexible strap 32 one end of which is fixedly connected to the reducing portion end 26 of the foundation 14 and the other end is adjustably connected to a connector 34, which is described more completely below, which is attached to the support end 28 of the foundation. The strap 32 is about nine inches long and is partly covered with VELCRO material which will form a strong lock when two locking VELCRO surfaces are pushed together. All the VELCRO is on the one side of the strap 32, the side initially away from the hand. The portion of the strap 32 near the fixed attachment point is one type of VELCRO, while the remainder of the strap is covered by the complementary type of VELCRO so that the strap can be passed through a loop or eyelet, be doubled back, and be attached to itself.

The connector 34 is a C-shaped piece of leather, or other strong flexible material, rivetted to the two projecting sections 30 of the foundation 14. At a midpoint of the connector 34, on a side furthest from the projecting sections 30, is located an eyelet 36 through which the flexible strap 32 can be passed. By using VELCRO material on the strap 32, the strap may passed through the eyelet 36, be pulled until the foundation 14 is firmly in place on the hand 20, and then pushed onto itself so that the VELCRO will hold it in position. The wide flexible connector 34 prevents the chafing which might occur were the strap to be attached directly to the support end 28. The connector 34 spreads the attaching force over a wide area and also permits a certain amount of movement as the hand bends and in this way increases the comfort of the splint 10 to the wearer.

The pressure plate 16, used to force the broken metacarpal 12 back into position is adjustably connected to the foundation 14 by being attached to the lower end of a threaded shaft 38 which passes through a complementary threaded aperture 40 in the reducing portion 26 of the foundation. The reducing portion 26 adjacent to the aperture 40 is strengthened by the addition a cylindrical shoulder 43 around the aperture. A knob 42 attached to the upper end of the threaded shaft 38 permits the pressure plate 16 to be adjusted. When the pressure plate 16 is adjusted inwardly toward the dorsum 13, it acts to reduce the peak 15 of the fracture and push the broken portions of the metacarpal 12 into their proper position.

When the splint is used, the pressure plate 16 is adjusted to a position nearly adjacent the foundation 14 and the foundation is placed on the hand 20. The strap 32 is pulled comfortably tight and then gripped into place by pressing the VELCRO surfaces together.

When the foundation 14 is in place, the knob 42 is turned to advance the pressure plate 16 toward the dorsum 13. The pressure plate 16 is advanced until the peak 15 of the broken metacarpal is pressed flat. Preferably, the pressure plate 16 is advanced until its force is as strong as the patient can bear. Of course, the pressure plate 16 can be adjusted by the patient as desired to alleviate pain or increase the pressure.

From the foregoing, it will be appreciated that the splint 10 of the invention allows a doctor to set a boxer's fracture of the fifth metacarpal and thereby prevent a deformity that has been characteristic in the healing of such fractures. The plate can also be used to maintain the fracture position after the broken metacarpal has been reduced by the surgeon. Moreover, the splint 10 provides a small, lightweight, inexpensive and fully adjustable device for reducing such fractures.

While a particular form of the invention has been illustrated and described, it will be apparent that various modifications can be made without departing from the spirit and scope of the invention.

I claim:

1. An apparatus for reducing a fracture of the metacarpal comprising:
   a generally rigid foundation having a reducing portion overlying the dorsum of the hand adjacent at least one metacarpal of said hand, said reducing portion being generally coplanar to said dorsum, and a support portion whose longitudinal cross section has a curved shape that is shaped complementary to the ulnar side of said hand, said support portion extending from said dorsum around said ulnar side of said hand and terminating in a support end, said support end being generally coplanar to the palm of said hand and having a width that exceeds the width of said reducing portion;
   means for securing said foundation to said hand, said means being adjustable to compensate for variations in sizes of hands; and
   means for reducing the apex of said fracture, said means comprising a threaded shaft mounting at an upper end an adjusting knob and an aperture in said reducing portion of said foundation adapted to receive said shaft connected to said reducing portion and mounting at a lower end adjacent said hand a pressure distributing plate, said means adapted for adjustable advancement of said plate from a first position adjacent said reducing portion to at least one other position further below said reducing end.

2. The apparatus described in claim 1, wherein said means for securing comprises:
   a flexible strap fixedly secured at one end to said reducing portion and adjustably secured to another segment of said splint.

3. The apparatus described in claim 2, further comprising:
   a flexible connector attached on one side to said support end and having on a second side an eyelet adapted to receive said strap; and
   adjustable means for securing said strap to said eyelet.

4. The apparatus described in claim 3 wherein adjustable means for securing comprises a VELCRO segment on said strap.

5. An apparatus for reducing a fracture of the metacarpal comprising:
   a foundation having a reducing portion overlying the dorsum of the hand adjacent to at least one metacarpal, and a support portion extending from said dorsum around the ulnar side of said hand and terminating in a support end;

means for reducing the apex of said fracture, said means connected to said reducing portion and mounting at a lower end adjacent said hand a pressure distributing plate, said means adapted for adjustable advancement of said plate from a first position adjacent said reducing portion to at least one other position displaced from said reducing portion toward said dorsum of said hand;

a flexible strap fixedly secured at one end to said reducing portion and adjustably secured at one end to said reducing portion and adjustably secured to another segment of said splint;

a flexible connector attached on one side to said support end and having on a second side an eyelet adapted to receive said strap;

adjustable means for securing said strap to said eyelet; and a set of projecting sections extending outwardly of the distal end of said support end, said connector being attached to said projecting sections.

6. The apparatus described in claim 5, wherein said pressure distributing plate is U-shaped and has a length of about ¾ inch.

7. An apparatus for reducing a fracture of the metacarpal comprising:

a foundation having, a reducing portion overlying the dorsum of the hand adjacent at least one metacarpal of said hand and having therethrough a threaded aperture, said aperture surrounded by a strengthening shoulder, said reducing portion having a width of about one inch, a support end coplanar to the palm of the hand, having extending from a distal end thereof two projecting sections, said support end having a width in excess of two inches, and a support portion connecting said support end and reducing portion, the longitudinal cross section of said support portion having a C-shaped curve complementary to the curve of the ulnar side of the hand;

a flexible connector attached along one side to said two projecting sections and having on a second side an eyelet;

a flexible strap having a VELCRO segment, said strap being fixedly attached at a first end to said reducing portion, one type of said VELCRO being located on the outside of said first end of said strap and a complementary attaching type VELCRO being located on the remainder of said side of said strap, and strap sized to pass through said eyelet;

a pressure plate having a U-shaped curve and being about one inch long; and a threaded shaft passing through said threaded aperture, said shaft movably mounting at an end thereof toward said support end said pressure plate, and mounting at its other end a knob.

8. A method for reducing a fracture of the metacarpal wherein said fractured portion extends above the normal location of said metacarpal in a direction toward the dorsum of a human hand, said method comprising:

positioning a rigid foundation having a support portion extending from said dorsum around the ulnar side of said hand and terminating in a support end, the longitudinal cross section of said support portion being generally curved shaped and complementary to said ulnar side of said hand, said support portion terminating in a support end whose width exceeds the width of said reducing portion, said reducing portion having an aperture therethrough to receive a threaded shaft mounting at an upper end an adjusting knob and at a lower end whose width exceeds the width of said reducing portion, said reducing portion having an aperture therethrough to receive a threaded shaft mounting at an upper end an adjusting knob and at a lower end a generally rectangular pressure plate, slightly curved along its width;

attaching said foundation to said hand using a flexible strap fixedly attached at one end to said foundation and adjustably attached to a flexible connector attached along one said to said support end and having on a second side an eyelet adapted to receive said strap; and adjusting said pressure plate in a direction toward said dorsum to a position at which said plate pushes said fractured portion of said metacarpal back into the position said metacarpal would occupy in a normal, unfractured state.

9. The apparatus described in claim 5 wherein the adjustable means for securing comprises a VELCRO segment on said strap.

* * * * *